US00PP24813P2

(12) United States Plant Patent
Barbour

(10) Patent No.: US PP24,813 P2
(45) Date of Patent: Aug. 26, 2014

(54) OAK TREE NAMED 'BETTERRED'

(50) Latin Name: *Quercus nuttallii*
Varietal Denomination: Betterred

(75) Inventor: John Hinds Barbour, Hawkinsville, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 7 days.

(21) Appl. No.: 13/507,453

(22) Filed: Jun. 30, 2012

(51) Int. Cl.
*A01H 5/00* (2006.01)

(52) U.S. Cl.
USPC ..... Plt./225

(58) Field of Classification Search
USPC ..... Plt./225
See application file for complete search history.

*Primary Examiner* — Annette Para
(74) *Attorney, Agent, or Firm* — C. A. Whealy

(57) ABSTRACT

A new and distinct cultivar of Oak tree named 'Betterred', characterized by its upwardly sweeping lateral branches forming a pyramidal plant form; vigorous growth habit; and glossy dark purple-colored leaves that maintain glossy dark coloration into the early summer.

9 Drawing Sheets

Botanical designation: *Quercus nuttallii*.
Cultivar denomination: 'BETTERRED'.

BACKGROUND OF THE INVENTION

The present invention relates to a new and distinct cultivar of Oak tree, botanically known as *Quercus nuttallii*, commercially referred to as Nuttall Oak or Red Oak and hereinafter referred to by the name 'Betterred'.

The new Oak tree originated from an open-pollination in Oconee County, Ga. of an unnamed selection of *Quercus nuttallii*, not patented, as the female, or seed, parent with an unknown selection of *Quercus nuttallii* as the male, or pollen, parent. The new Oak tree was discovered and selected by the Inventor as a single plant from within the progeny of the stated open-pollination in a controlled greenhouse environment in Oconee County, Ga. in May, 2007.

Asexual reproduction of the new Oak tree by softwood cuttings in a controlled environment in Oconee County, Ga. since 2008 has shown that the unique features of this new Oak tree are stable and reproduced true to type in successive generations.

SUMMARY OF THE INVENTION

Trees of the new Oak have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Betterred'. These characteristics in combination distinguish 'Betterred' as a new and distinct Oak tree:

1. Upwardly sweeping lateral branches forming a pyramidal plant form.
2. Vigorous growth habit.
3. Glossy dark purple-colored leaves that maintain glossy dark coloration into the early summer.

Trees of the new Oak can be compared to plants of the female parent selection. Trees of the new Oak differ primarily from trees of the female parent selection in branch orientation as trees of the new Oak have more upwardly sweeping lateral branches than trees of the female parent selection.

Trees of the new Oak can also be compared to plants of *Quercus nuttallii* 'QNSTD', disclosed in U.S. Plant Pat. No. 16,254. Trees of the new Oak and 'QNSTD' differ primarily in branch orientation and plant form as trees of the new Oak have upwardly sweeping lateral branches whereas trees of 'QNSTD' have laterally-orientated lateral branches.

BRIEF DESCRIPTION OF THE PHOTOGRAPHS

The accompanying colored photographs illustrate the overall appearance of the new Oak tree showing the colors as true as it is reasonably possible to obtain in colored reproductions of this type. Colors in the photographs may differ slightly from the color values cited in the detailed botanical description which accurately describe the colors of the new Oak tree.

The photographs on the first sheet comprise side perspective views of typical trees of 'Betterred' and 'QNSTD' grown during the winter in an outdoor nursery showing the differences in branch orientation and plant form.

The photograph on the second sheet comprises a side perspective view of a typical tree of 'Betterred' grown during the spring in an outdoor nursery.

The photograph on the third sheet is a close-up view of the upper surface of typical leaves of 'Betterred' grown during the spring.

The photograph on the fourth sheet is a close-up view of the lower surface of typical leaves of 'Betterred' grown during the spring.

The photograph on the fifth sheet is a close-up view of the upper surface of typical leaves of 'Betterred' grown during the summer.

The photograph on the sixth sheet is a close-up view of the lower surface of typical leaves of 'Betterred' grown during the summer.

The photograph on the seventh sheet is a close-up view of a typical tree of 'Betterred' grown during the spring in an outdoor nursery.

The photograph on the eighth sheet is a close-up view of a typical tree of 'Betterred' grown during the autumn in an outdoor nursery.

The photograph on the ninth sheet is a close-up view of a section of trunk of a typical tree of 'Betterred' grown in an outdoor nursery.

DETAILED BOTANICAL DESCRIPTION

The aforementioned photographs and following observations, measurements and values describe plants grown in an outdoor nursery in Pulaski County, Ga. and under cultural practices typical of Oak tree commercial production. Trees were four years old when the photographs and description were taken. In the following description, color references are made to The Royal Horticultural Society Colour Chart, 2007 Edition, except where general terms of ordinary dictionary significance are used.

Botanical classification: *Quercus nuttallii* 'Betterred'.

Parentage:

*Female, or seed, parent*.—Unnamed selection of *Quercus nuttallii*, not patented.

*Male, or pollen, parent*.—Unknown selection of *Quercus nuttallii*, not patented.

Propagation:

*Type*.—By softwood cuttings.

*Root description*.—Fibrous.

*Time to rooting*.—About three to four weeks.

Plant description:

*Plant form and growth habit*.—Upright tree with upwardly sweeping lateral branches forming a pyramidal plant form; freely branching habit with numerous lateral branches developing per plant; vigorous growth habit; flowers have not been observed on plants of the new Oak tree.

*Plant height*.—About 7.92 meters.

*Plant diameter*.—About 4.27 meters.

*Height to width ratio*.—About 1.9.

*Branch orientation*.—Lower canopy branches, about 43° from central leader; upper canopy branches, about 31° from central leader.

*Lateral branch color*.—Developing branches, close to N77A; mature branches, close to between 166A and 152A mottled with close to 198D.

*Trunk diameter, about* 15 *cm above ground level*.—About 18.42 cm.

*Immature bark*.—Texture: Smooth, glabrous. Color: Close to 198A with patches of close to 198D. Lenticels: Arrangement: Scattered or in vertical strands. Length: About 3 mm. Color: Close to 199D.

*Mature bark*.—Texture: Rough with shallow ridges and furrows. Color: Close to 198A with patches of close to 198D.

*Leaf arrangement*.—Alternate, simple.

*Leaf length*.—About 10.2 cm to 22.9 cm.

*Leaf width*.—About 5.1 cm to 12.7 cm.

*Leaf shape*.—Roughly ovate to elliptic with five to nine deep narrow lobes; margins, entire; sinuses rounded; apex, acute to acuminate; base, attenuate; venation, pinnate.

*Leaf texture, upper and lower surfaces*.—Smooth, glabrous.

*Leaf luster, upper and lower surfaces*.—Glossy.

*Leaf color, spring*.—Upper surface: Close to N77A. Lower surface: Close to 146A and N77A.

*Leaf color, summer*.—Upper surface: Close to 137A. Lower surface: Close to 146A.

*Leaf color, autumn*.—Upper and lower surfaces: Close to 13B, 47A and 22A.

*Leaf petioles*.—Length: About 1.59 cm to 2.22 cm. Texture, upper and lower surfaces: Smooth, glabrous. Color, upper and lower surfaces: Close to N77A.

*Leaf buds*.—Length: About 3.18 cm to 6.35 cm. Texture: Pubescent; margins, ciliate. Color: Close to 200C mottled with close to 198D.

Winter hardiness: Trees of the new Oak have been observed to be hardy to USDA Hardiness Zone 8a.

Pathogen & pest resistance: Trees of the new Oak have been not observed to be resistant to pathogens and pests common to Oak trees.

It is claimed:

1. A new and distinct Oak tree named 'Betterred' as illustrated and described.

* * * * *

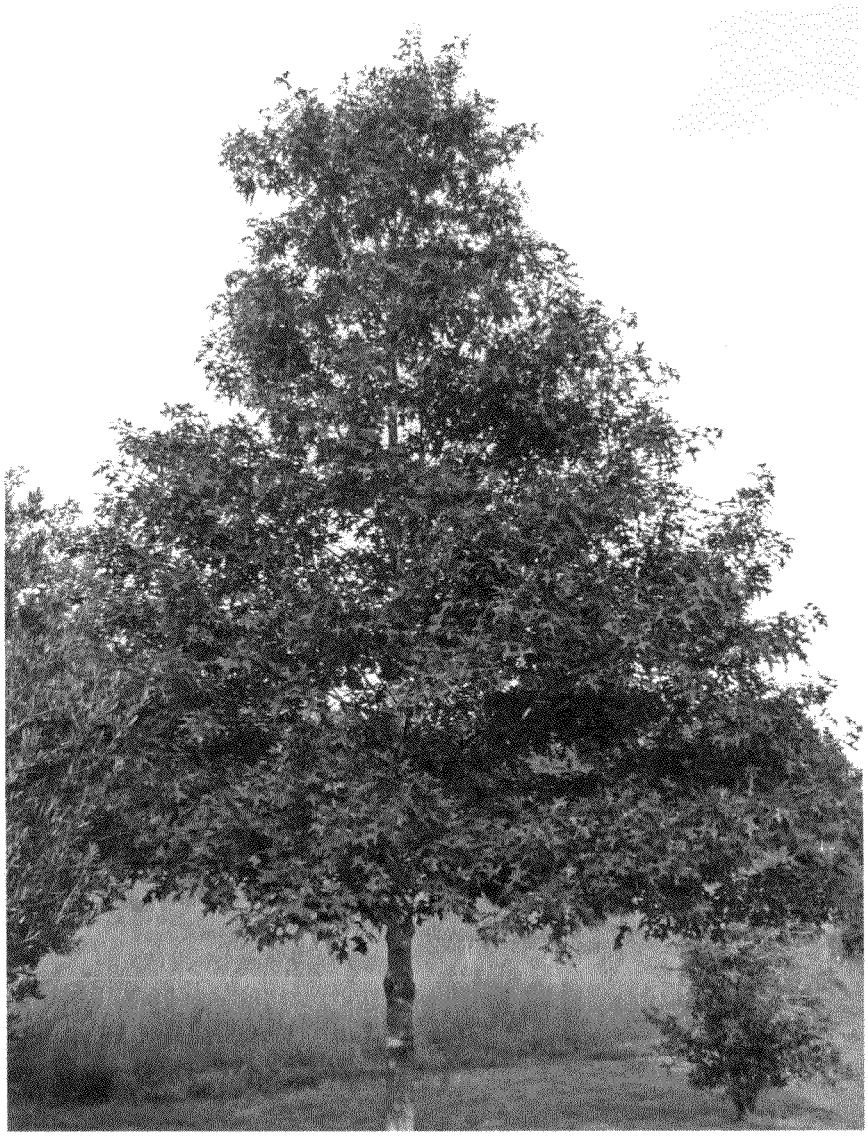

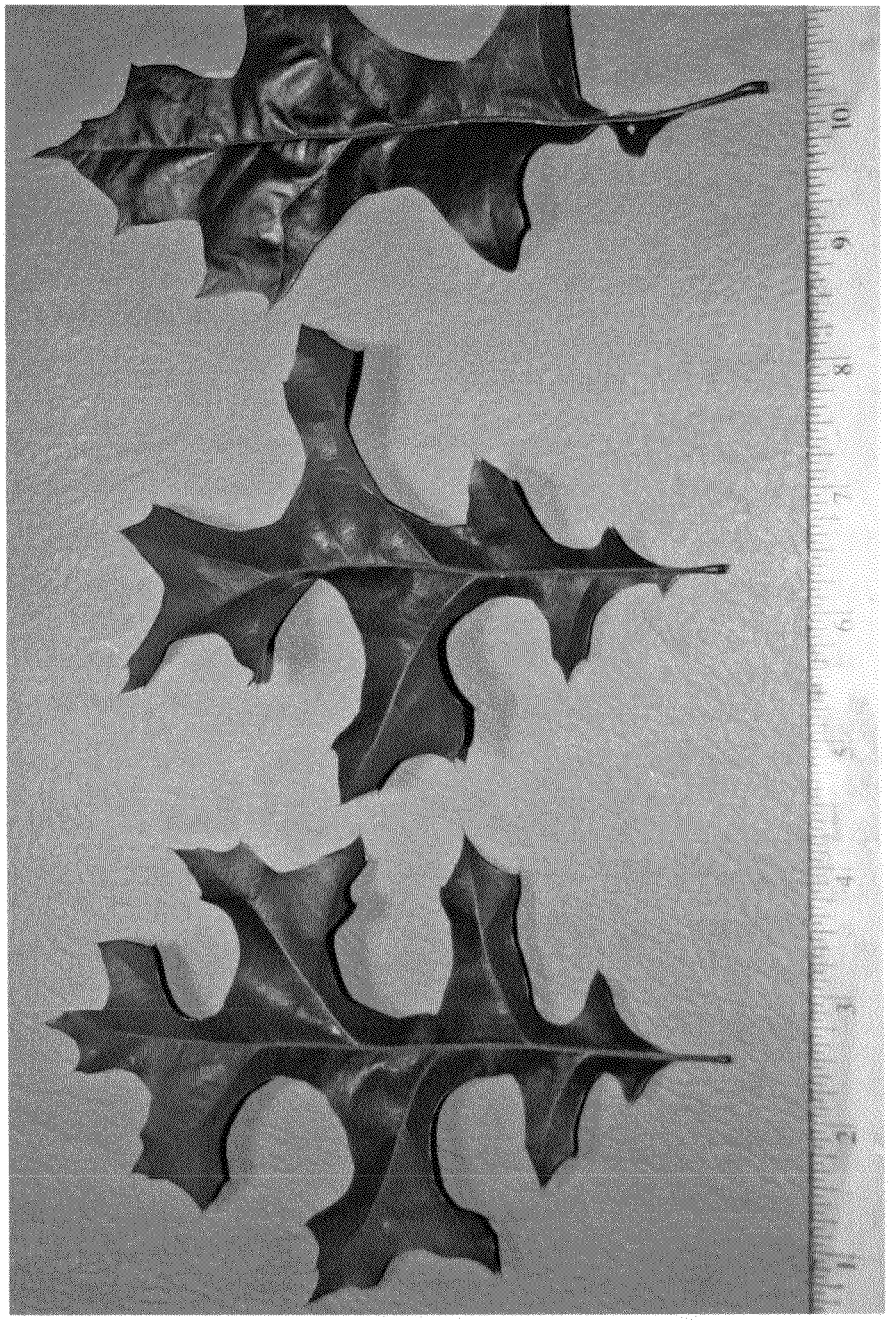

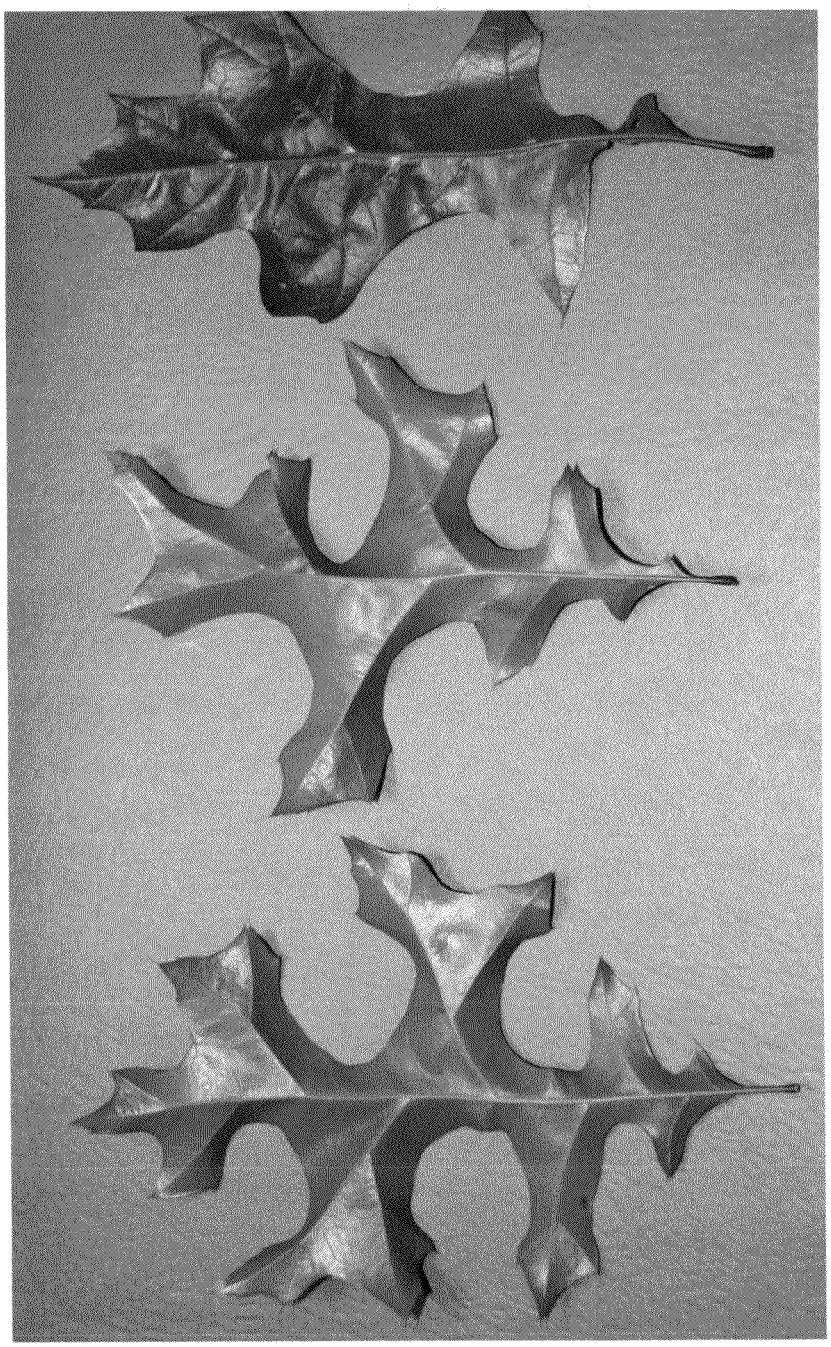

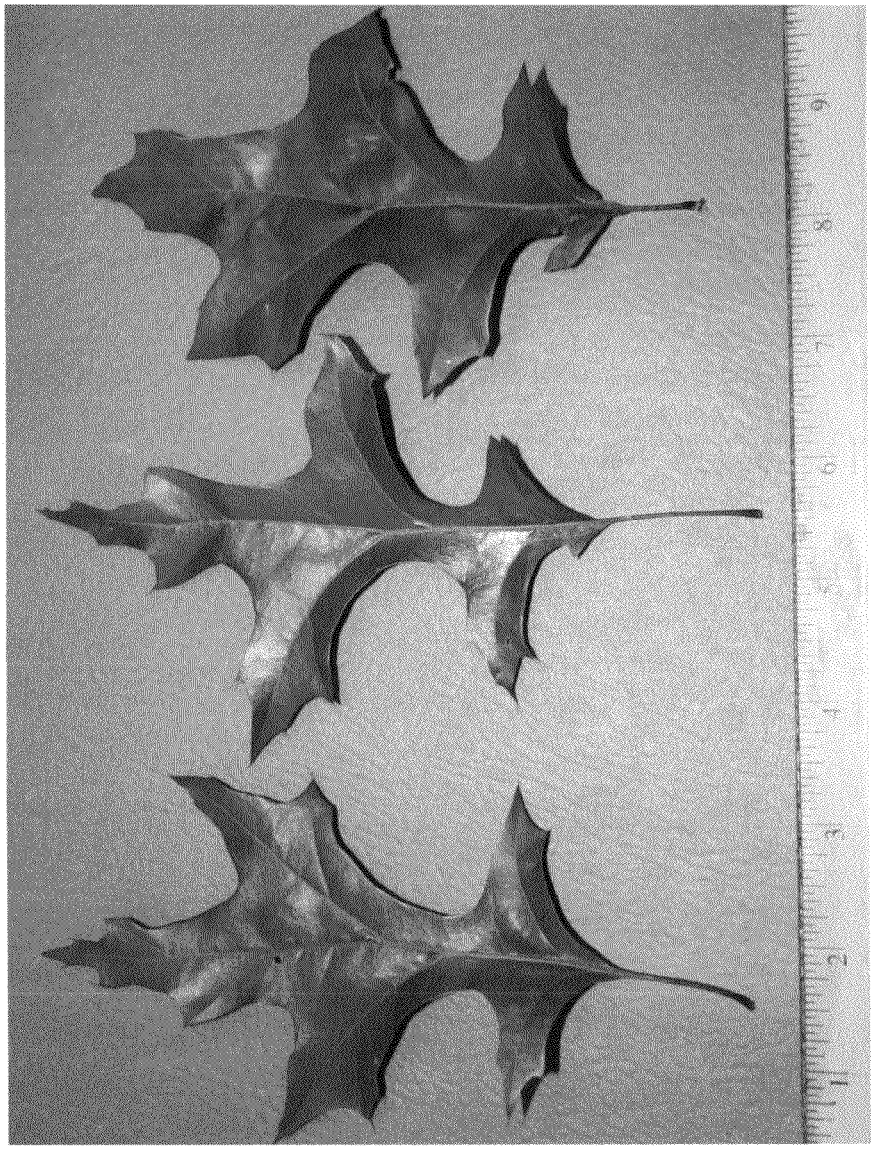

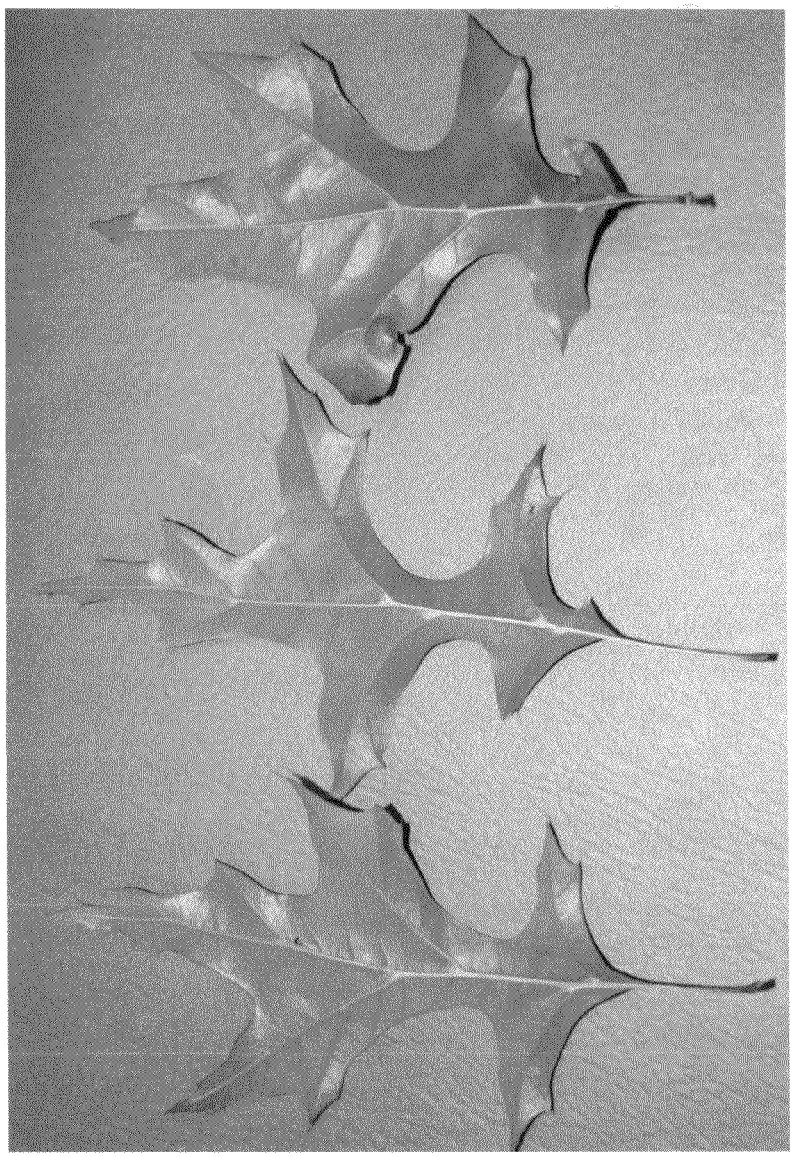

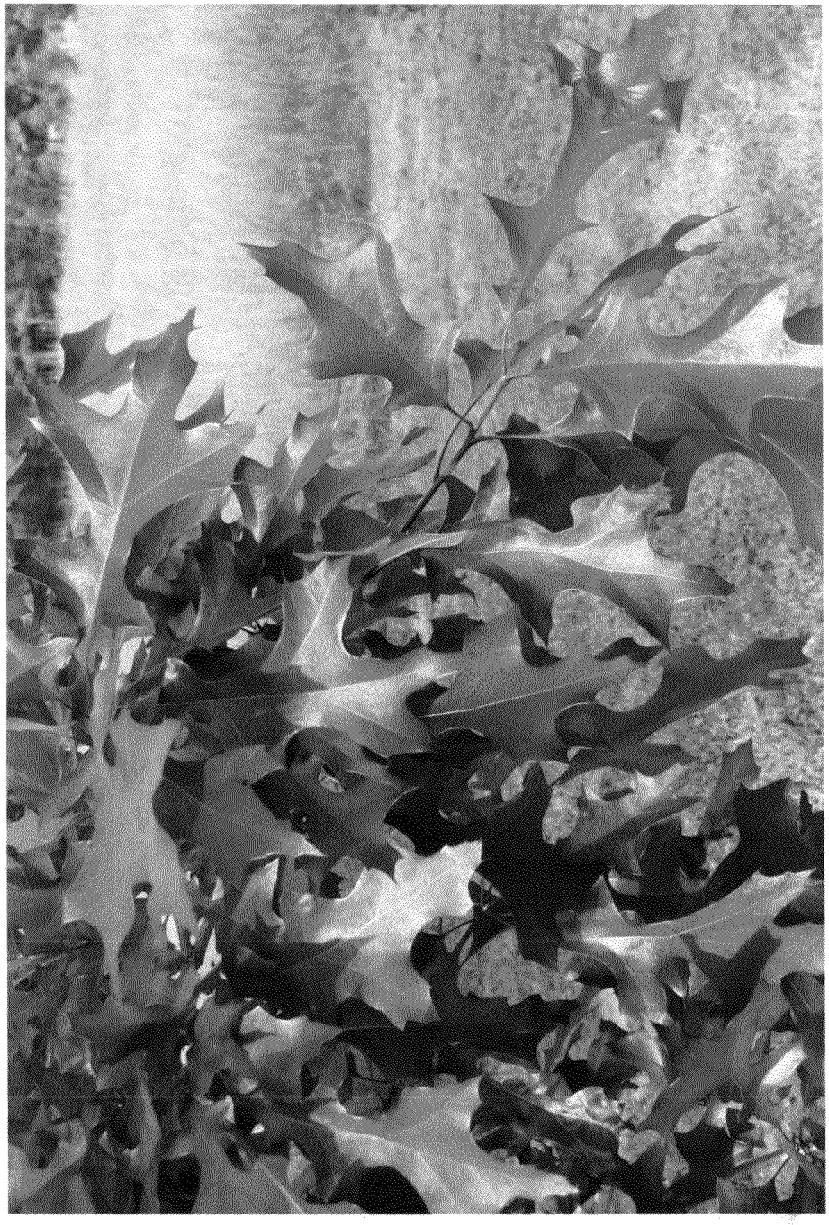

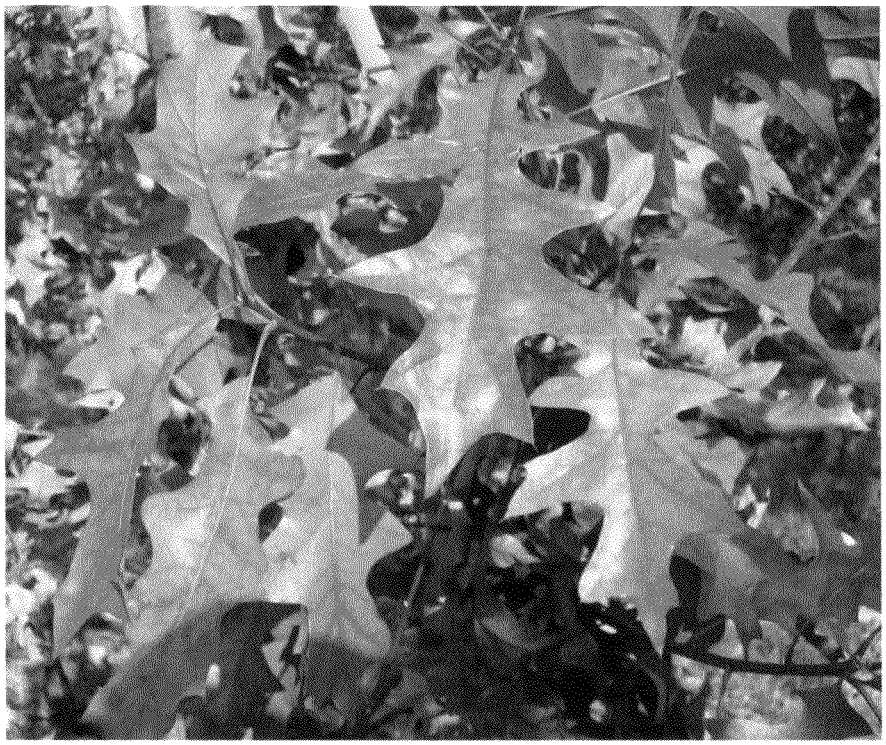

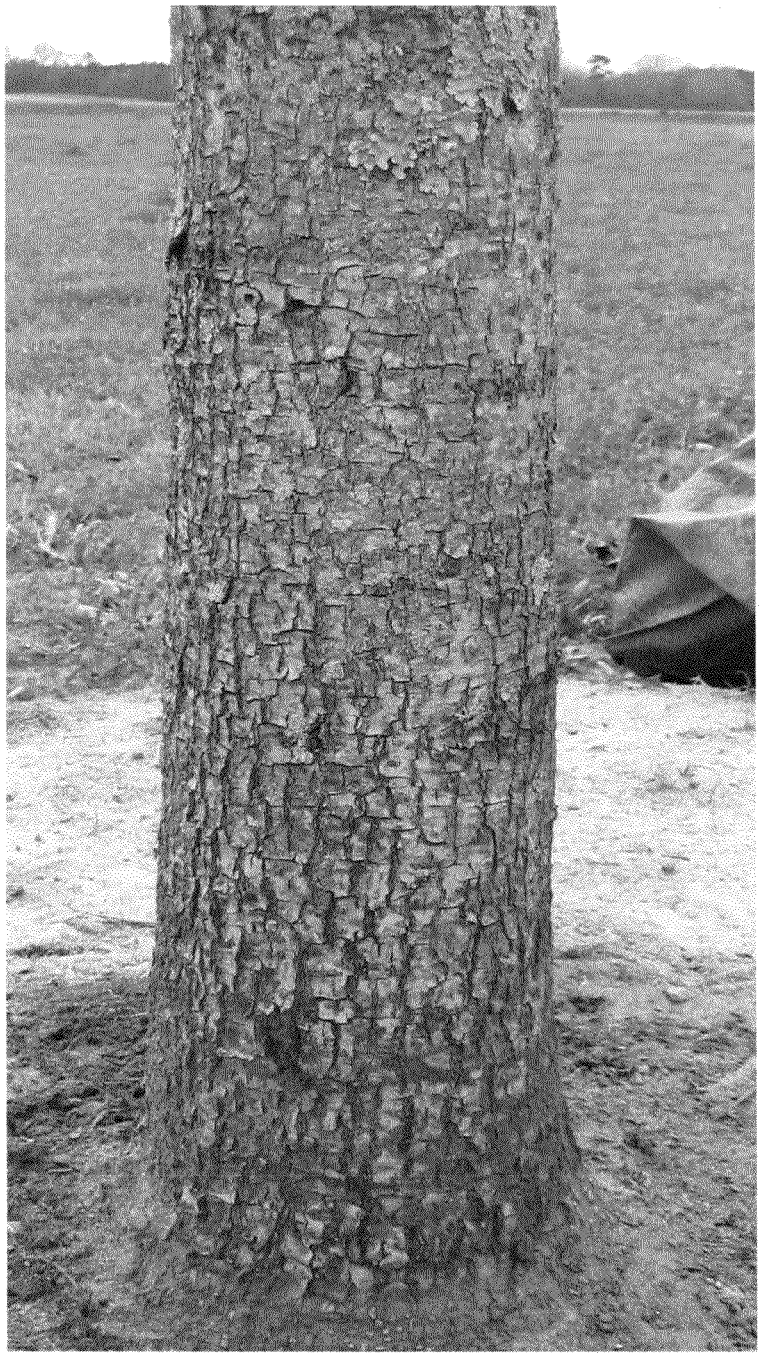

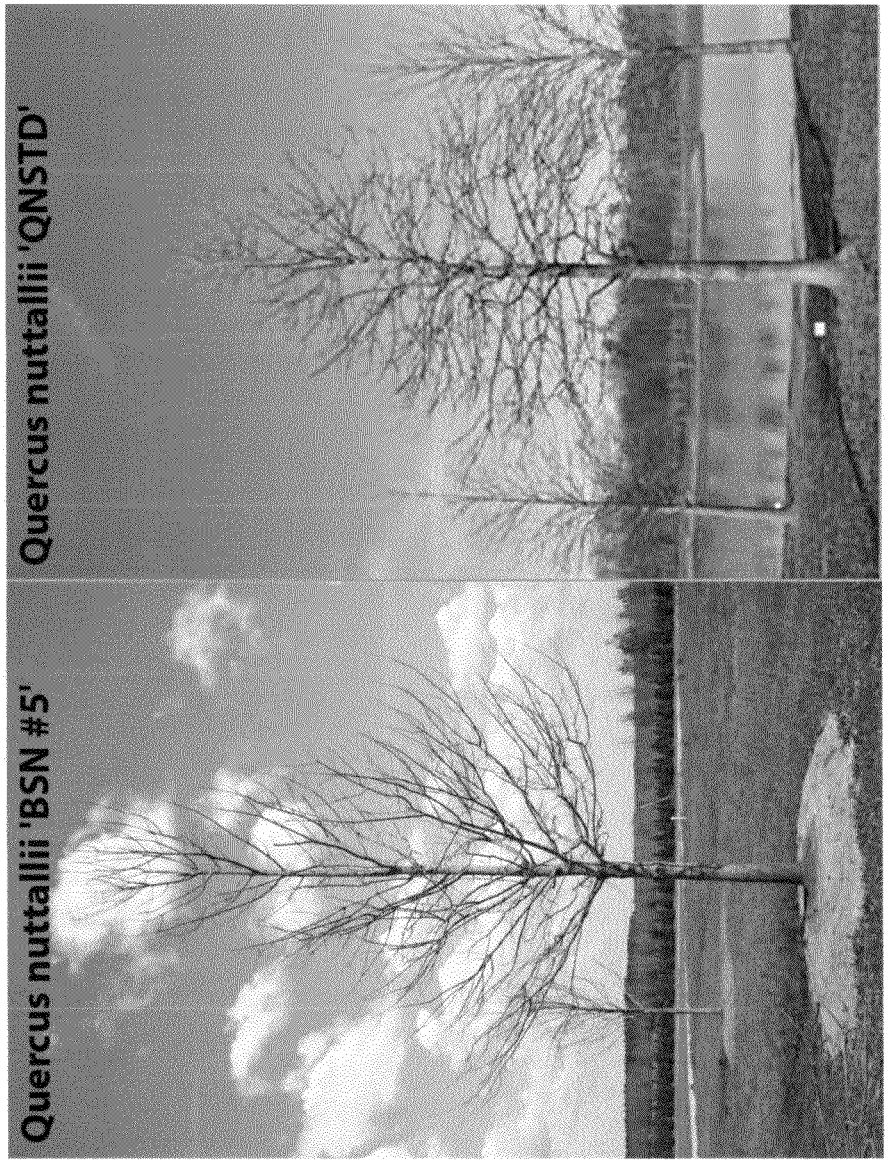
Quercus nuttallii 'BSN #5'
Quercus nuttallii 'QNSTD'